(12) United States Patent
Dubois et al.

(10) Patent No.: US 12,592,311 B2
(45) Date of Patent: Mar. 31, 2026

(54) SYSTEMS AND METHODS FOR PERFORMING OPTIMAL ANCHOR-PRIOR MATCHING OPERATIONS

(71) Applicant: Optum, Inc., Minnetonka, MN (US)

(72) Inventors: David Dubois, Mirabel (CA); Sara Daneshvar, Port Moody (CA); Paul Alain Vial, Vancouver (CA); Jaime Lea Ekis, Charlotte, NC (US)

(73) Assignee: Optum, Inc., Minnetonka, MN (US)

( * ) Notice: Subject to any disclaimer, the term of this patent is extended or adjusted under 35 U.S.C. 154(b) by 329 days.

(21) Appl. No.: 18/301,624

(22) Filed: Apr. 17, 2023

(65) Prior Publication Data

US 2024/0347171 A1      Oct. 17, 2024

(51) Int. Cl.
| | |
|---|---|
| *G06K 9/00* | (2022.01) |
| *G06T 7/00* | (2017.01) |
| *G16H 30/20* | (2018.01) |
| *G16H 30/40* | (2018.01) |

(52) U.S. Cl.
CPC ........... *G16H 30/40* (2018.01); *G06T 7/0014* (2013.01); *G16H 30/20* (2018.01); *G06T 2200/24* (2013.01); *G06T 2207/20081* (2013.01); *G06T 2207/20084* (2013.01); *G06T 2207/30004* (2013.01); *G06T 2207/30168* (2013.01)

(58) Field of Classification Search
CPC ........ G16H 30/40; G16H 30/20; G16H 50/70; G06T 7/0014; G06T 2200/24; G06T 2207/20081; G06T 2207/20084; G06T 2207/30004; G06T 2207/30168
See application file for complete search history.

(56) References Cited

U.S. PATENT DOCUMENTS

| | | | |
|---|---|---|---|
| 2019/0286652 A1* | 9/2019 | Habbecke | ........... G06F 16/7837 |
| 2021/0158933 A1 | 5/2021 | Frosch et al. | |
| 2021/0398650 A1 | 12/2021 | Baker et al. | |

FOREIGN PATENT DOCUMENTS

| | | | | |
|---|---|---|---|---|
| CN | 114732431 A | * | 7/2022 | ............. G06N 3/045 |
| CN | 114842003 A | * | 8/2022 | ............. G06T 7/194 |
| WO | WO-2023/274599 A1 | | 1/2023 | |
| WO | WO-2024016691 A1 | * | 1/2024 | ........... G06V 10/774 |

OTHER PUBLICATIONS

Extended European Search Report for Application No. 24164436.8, dated Sep. 10, 2024.

* cited by examiner

*Primary Examiner* — Xin Jia
(74) *Attorney, Agent, or Firm* — MARSHALL, GERSTEIN & BORUN LLP

(57)      ABSTRACT

Systems, methods, and apparatuses implementing a display optimization system are provided herein. In some embodiments, an example display optimization system may be configured to perform an optimal anchor-prior matching operation to identify optimal anchor-prior image pairs or series pairs from new medical imaging data (e.g., one or more anchor image series) and historical medical imaging data (e.g., one or more prior image series).

20 Claims, 6 Drawing Sheets

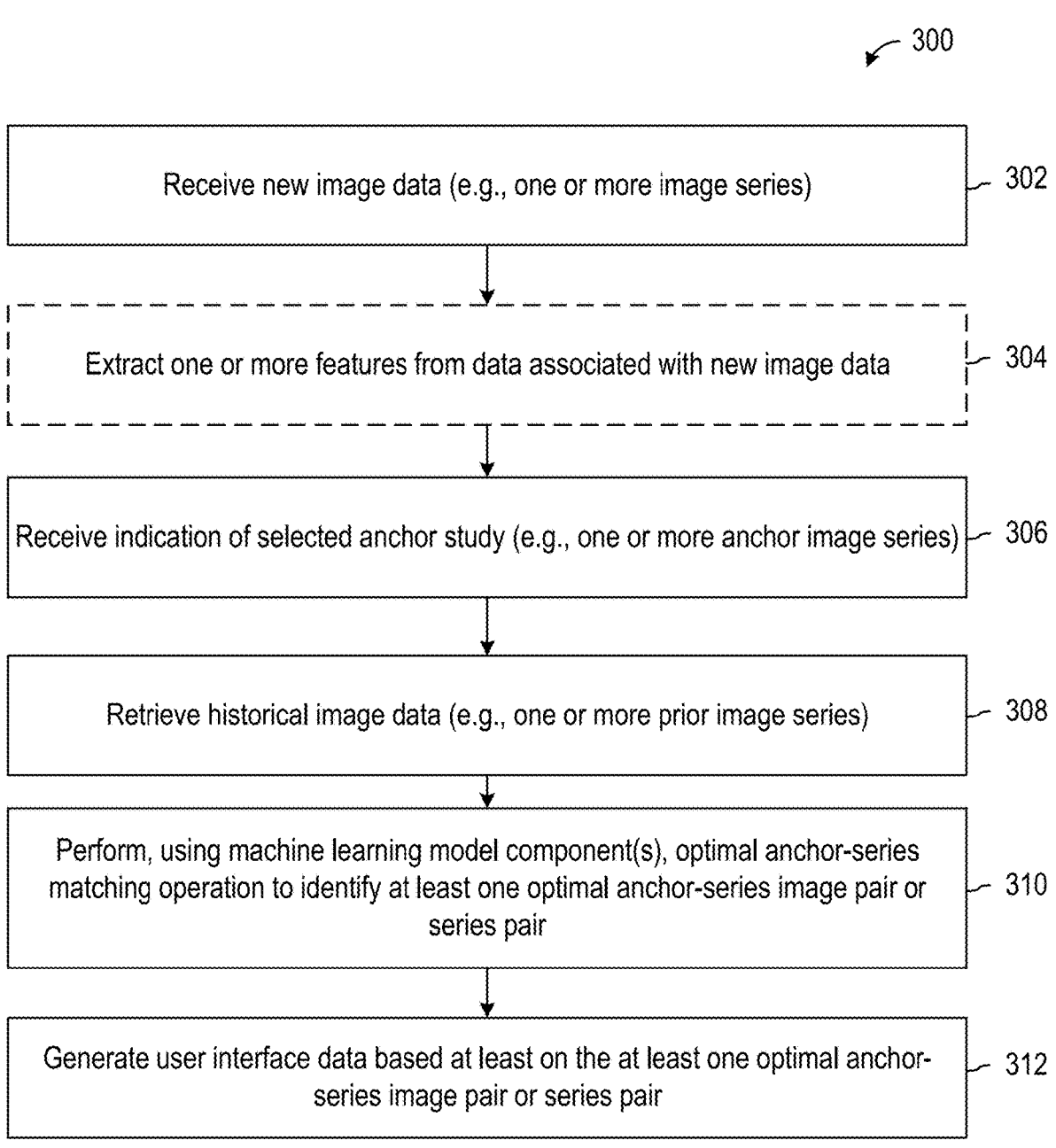

300

Receive new image data (e.g., one or more image series) — 302

Extract one or more features from data associated with new image data — 304

Receive indication of selected anchor study (e.g., one or more anchor image series) — 306

Retrieve historical image data (e.g., one or more prior image series) — 308

Perform, using machine learning model component(s), optimal anchor-series matching operation to identify at least one optimal anchor-series image pair or series pair — 310

Generate user interface data based at least on the at least one optimal anchor-series image pair or series pair — 312

| Anchor Series | Prior Series | Score for ranking (higher = better match) |
|---|---|---|
| A1 | P1 | 0.9 |
| A1 | P2 | 0.5 |
| A1 | P3 | 0.6 |
| A1 | P4 | 0.1 |
| A2 | P1 | 0.7 |
| A2 | P2 | 0.4 |
| A2 | P3 | 0.8 |
| A2 | P4 | 0.3 |
| A3 | P1 | 0.9 |
| A3 | P2 | 0.3 |
| A3 | P3 | 0.5 |
| A3 | P4 | 0.8 |

FIG. 4A

SYSTEMS AND METHODS FOR PERFORMING OPTIMAL ANCHOR-PRIOR MATCHING OPERATIONS

BACKGROUND

Picture archiving and communication systems (PACS) are medical imaging systems that can be configured to provide access to medical images across a variety of imaging modalities and devices including X-ray plain film (PF), ultrasound (US), endoscopy (ES), mammograms (MG), positron emission tomography (PET), computed tomography (CT), and magnetic resonance imaging (MRI). An example PACS can comprise image data, a secured network, workstations and computing devices, and storage archives. Digital Imaging and Communications in Medicine (DI-COM) defines a universal standard for the communication and management of medical imaging data. In particular, DICOM information object definitions encode data from a plurality of imaging device types (e.g., CT, MRI, US, and the like) and may be utilized by computing devices to facilitate data visualization and medical diagnostics.

Medical professionals (e.g., radiologists) may review image data using a PACS and may further configure a display or viewport or manipulate images within the viewport (e.g., zoom, level, measure, position in a particular location in a viewport, and the like) while conducting the review. Configuring displays in this manner is time consuming and inefficient. For example, a radiologist reviewing a new or current ("anchor") study may want to review relevant prior studies alongside the current study. Each study can comprise one or more series of multiple images, each with a different area of interest. For example, the radiologist may want to review a relevant image in a series of images from the study, and a relevant spot within that image. Radiologists today create display protocols (e.g., "hanging protocols") that define how images are displayed (e.g., dividing a screen layout into viewports and placing image series in viewports). One existing solution is leveraging rule-based engines for setting up viewports. These rule-based engines often rely on metadata (e.g., DICOM tags) to determine how images should be displayed and/or oriented in a viewport (e.g., axial, sagittal, coronal, or the like). The metadata can be numerical, categorical, or manually-entered text. The metadata may include optional fields and mandatory fields and the structure of the values is generally determined by device manufacturers and technicians. However, rule-based engines are often fragile and can be broken by small changes to the metadata. Moreover, much of the DICOM data that current rule-based engines rely on may be entered by hand by technicians, which can be unreliable (e.g., due to human error). More importantly, rule-based engines are often unreliable for identifying related images in the context of, for example, placing a prior image series and an anchor image series in viewports for comparison. By way of example, if the anchor image series was captured using a first machine type and the prior image series was captured using a second machine type that is different from the first machine type, the DICOM data nomenclature may be different such that a rules-based engine is unable to correctly associate the anchor image series with the prior image series which may necessitate extensive searching and viewport manipulation by a medical professional.

Therefore, systems and methods are desired that overcome challenges in the art, some of which are described above.

SUMMARY

To overcome these challenges, embodiments of the present disclosure automatically and dynamically identify relevant images and can, for example, match an anchor image series and a prior image series within a display protocol. For example, a radiologist may prefer to see a current image series (e.g., of a head CT scan) that targets a particular type of tissue side-by-side with a previously captured image series that targets the same type of tissue. Accordingly, embodiments of the present disclosure improve the efficiency and speed of the review process by determining optimal matches between current and historical medical imaging data (e.g., a current image series and a prior image series) in a manner that does not require extensive searching by an end-user.

By utilizing some or all of the innovative techniques disclosed herein, various embodiments of the present disclosure reduce clinician workload when performing comparative reviews as well as underlying data retrieval operations associated therewith.

In some embodiments, a computer-implemented method for identifying at least one optimal anchor-prior image pair or series pair is provided. The computer-implemented method can comprise: receiving, by one or more processors, new medical imaging data; extracting, by the one or more processors, one or more features from the new medical imaging data; receiving, by the one or more processors, an indication of a selected anchor study comprising one or more anchor image series, wherein the selected anchor study comprises at least some of the new medical imaging data; retrieving, by the one or more processors, a prior study comprising one or more prior image series corresponding with the selected anchor study; performing, by the one or more processors and using one or more machine learning model components, an optimal anchor-prior matching operation based at least on the one or more extracted features associated with the one or more anchor image series and the one or more prior image series; and outputting, by the one or more processors, the at least one optimal anchor-prior image pair or series pair.

In accordance with another embodiment, a display optimization system is provided. The system can comprise: at least one computing device; and a memory storing computer-readable instructions that when executed by the at least one computing device cause the at least one computing device to: receive new medical imaging data; extract one or more features from the new medical imaging data; receive an indication of a selected anchor study comprising one or more anchor image series, wherein the selected anchor study comprises at least some of the new medical imaging data; retrieve a prior study comprising one ore more prior image series corresponding with the selected anchor study; perform, using one or more machine learning model components, an optimal anchor-prior matching operation based on the one or more extracted features associated with the one or more anchor image series and the one or more prior image series; and output at least one optimal anchor-prior image pair or series pair.

In accordance with yet another embodiment, a non-transitory computer-readable medium is provided. The non-transitory computer-readable medium can include computer-executable instructions stored thereon that when executed by at least one computing device cause the at least one computing device to: receive new medical imaging data; extract one or more features from the new medical imaging data; receive an indication of a selected anchor study comprising one or more anchor image series, wherein the selected anchor study comprises at least some of the new medical imaging data; retrieve a prior study comprising one or more prior image series corresponding with the selected anchor study; perform, using one or more machine learning model components, an optimal anchor-prior matching operation based at least on the one or more extracted features associated with the one or more anchor image series and the one or more prior image series; and output at least one optimal anchor-prior image pair or series pair.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

BRIEF DESCRIPTION OF THE DRAWINGS

Various objects, aspects, features, and advantages of the disclosure will become more apparent and better understood by referring to the detailed description taken in conjunction with the accompanying drawings, in which like reference characters identify corresponding elements throughout. In the drawings, like reference numbers generally indicate identical, functionally similar, and/or structurally similar elements.

FIG. 3 is a diagram illustrating an example method that includes performing an optimal anchor-prior matching operation, in accordance with certain embodiments of the present disclosure;

FIG. 4A is a table depicting an example output of a machine learning model;

DETAILED DESCRIPTION

Figure 1:
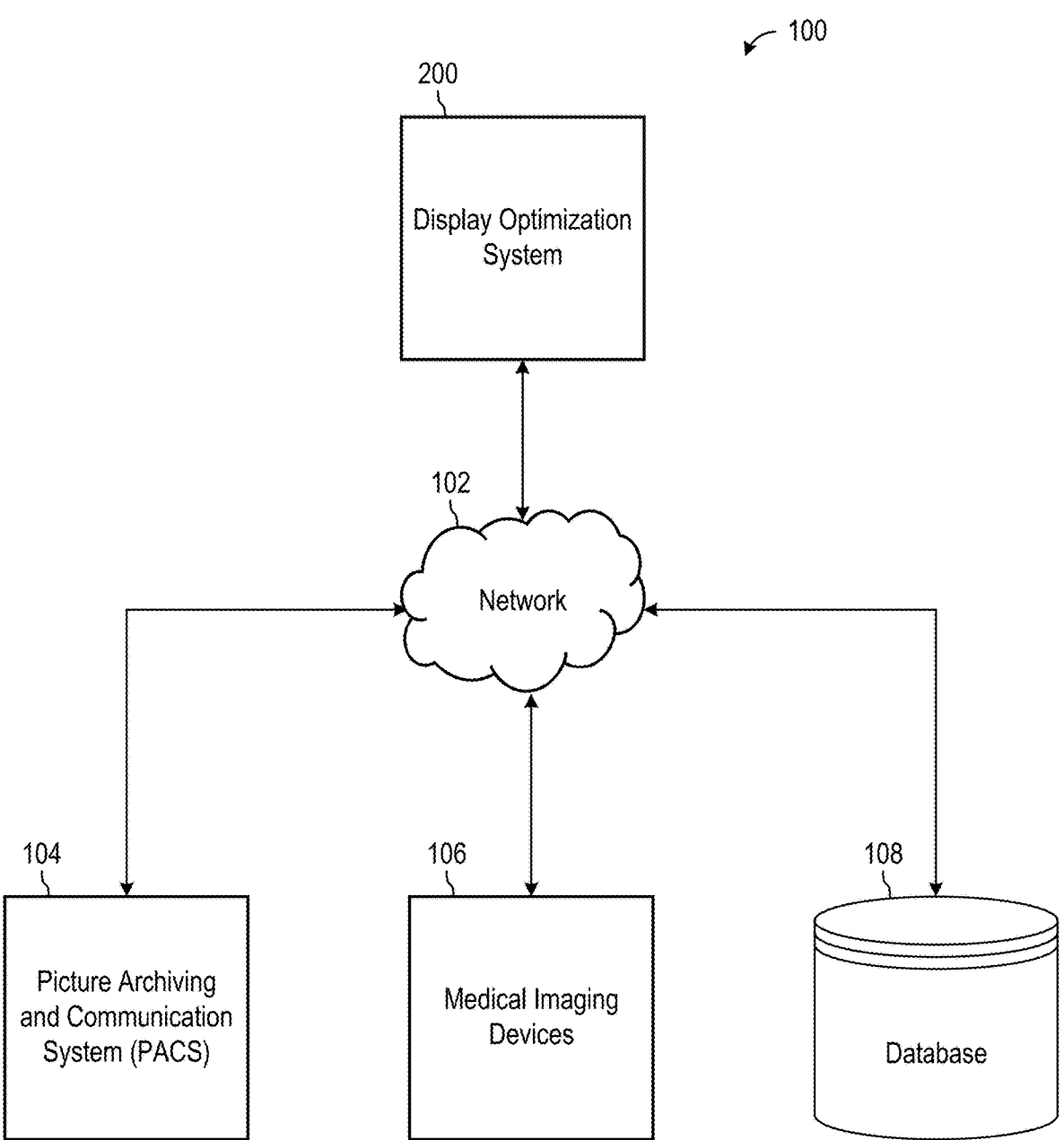
FIG. 1 is a block diagram of a system, in accordance with certain embodiments of the present disclosure.

Referring generally to the figures, a system and methods that include performing an optimal anchor-prior matching operation are shown, according to various embodiments. The process of reviewing a study (e.g., medical imaging data from a particular study) may require accessing related historical studies for comparison and manually configuring a display or viewport, for example, by zooming, searching, or dragging-and-dropping user interface elements, in order to review the results simultaneously. A study can comprise a plurality of series, where each series in turn comprises one or more images. Additionally, in some examples, a series can comprise a plurality of stacked images depicting multiple slices/images. As further discussed herein, new medical imaging data may comprise a current/anchor image series, study, or image(s) and historical medical imaging data may comprise a prior/reference series, study, or image(s).

As an example, a medical professional reviewing the results of an MRI scan may wish to view other related MRI scans, and their associated data, in parallel. In some cases, related studies may be shown with the subject MRI scan due to predefined display protocols, which are rules or instructions that determine how the images should be displayed and the layout of said images on a picture archiving and communication system (PACS) terminal or other type of imaging workstation. Accordingly, the medical professional and/or the PACS may search for a body region in other studies or may search for image series that have similar tags (e.g., use a similar MRI pulse sequence as the subject MRI scan). Many current technologies often rely on text-based searches using DICOM tags to identify related studies or images, which can yield undesirable results. For example, many different MRI pulse sequences can exist that provide similar information and MRI manufacturers often create their own unique pulse sequences and variations, which may have unique names, etc. Additionally, MRI pulse sequence data and/or MRI image metadata may often be entered by hand which can introduce human error into naming conventions and tags. Because of this, it can be difficult to locate related studies or MRI images based on manually-entered information in DICOM tags.

To address these shortcomings, the systems and methods described herein can automatically identify related images for use in conjunction with a display protocol for presenting a new study in parallel with one or more prior studies. Thus, a user (e.g., a medical professional) does not need to rely on the manual techniques to identify the most relevant historical images for viewing with a new study or series. In some embodiments, a machine learning model may be applied to new image data to extract features and identify various characteristics of the new image data. For example, the machine learning model may receive pixel data of an image and may output classifications for various characteristics associated with the image, which in turn can be stored with the image data and/or used to generate a custom DICOM tag for the image data. In some implementations, the extracted features and/or identified characteristics can be used in a subsequent anchor-prior matching operation to identify optimal matches (e.g., historical series or images) for viewing in parallel with a current study, series, or set of images. Additional features and benefits of this system and methods are described in greater detail below.

Turning first to FIG. 1, a block diagram of a system 100 for performing an optimal anchor-prior matching operation is shown, according to some embodiments. In particular, the system 100 may automatically process new image data (e.g., current MRI images), stored image data and metadata associated therewith. Such data can be used to perform an optimal anchor-prior matching operation in relation to at least a portion of the new image data (e.g., one or more anchor image series) and historical image data (e.g., one or more prior image series). It should be appreciated that, in some embodiments, the system 100 includes additional components that are not shown in FIG. 1, but that may be referenced below. Additionally, in some embodiments, the system 100 can include fewer or more components than those depicted in FIG. 1.

As shown, the system 100 can include a display optimization system 200 that handles the processing and analysis of image data. In some embodiments, the display optimization system 200 receives medical imaging data from at least one of medical imaging devices 106 and/or a database 108. As described herein, medical imaging data or image data may include both medical images (e.g., MRI scans or pictures) and corresponding metadata (e.g., time of capture, area of the body, and the like). Image data can also include one or more image series. The display optimization system 200 may process the image data by, in some embodiments, extracting features from the metadata, and subsequently using a machine learning model to process the features. Based on the operations of the display optimization system 200, the database 108 may be updated and/or a DICOM tag may be generated for the image data. The display optimization system 200 can store extracted features in conjunction with received and processed image data for subsequent operations. In some embodiments, the image data is processed when received from a medical imaging device 106. In other examples, image data can be processed in response to a trigger (e.g., radiologist selecting a study for review/ evaluation). Additional details of the system 200 are described in greater detail below with respect to FIG. 2.

Medical imaging devices 106, as mentioned above, may include any devices that are capable of capturing medical images. Example medical imaging devices 106 include X-ray machines, CT scanners, MRI machines, and the like. In some embodiments, the display optimization system 200 receives image data from medical imaging devices 106 via a network 102, as described below. In other embodiments, the image data is first stored in the database 108 before being retrieved by the display optimization system 200. Accordingly, the database 108 may be hosted on any suitable computing device, such as a server or workstation. In some embodiments, the database 108 is hosted on a remote device (e.g., a remote server), or a device that is external to the system 200. In other embodiments, the database 108 may be hosted on the system 200, as described below. In any case, the database 108 may be configured to store and maintain image data for later analysis and/or viewing.

In some embodiments, the image data is viewed on a picture archiving and communication system (PACS) 104. Accordingly, the PACS 104 may also be a computing device that is capable of receiving and displaying image data, such as a workstation, a desktop or laptop computer, a smart-phone, a tablet, etc. Generally, the PACS 104 may allow a user to interact with the display optimization system 200, and more broadly, the system 100. In some embodiments, the PACS 104 may include a graphical user interface that further includes at least one of a display (e.g., an LCD or LED display) and an input device (e.g., a touchscreen, a mouse, a keypad, etc.). For example, the PACS 104 may include a screen that can display images, as discussed in greater detail below.

The network 102, as mentioned above, is shown to communicably couple the display optimization system 200, PACS 104, medical imaging devices 106, and the database 108. Accordingly, the network 102 may be any suitable network that allows for data to be transferred between the components of the system 100. In some embodiments, the network 102 is a public network, such as the Internet. In other embodiments, the network 102 is a private network, such as a virtual private network (VPN). In yet other embodiments, the network 102 may include a plurality of public and private connections. For example, the network 102 may be a local area network (LAN), a wide area network (WAN), etc. To continue this example, the network 102 may be an internal network (e.g., a LAN) for a facility (e.g., a hospital) that allows the display optimization system 200, PACS 104, medical imaging devices 106, and the database 108 to exchange data and/or to access the Internet. It will also be appreciated that, in some embodiments, one or more components of the system 100 are remotely connected to one another. For example, the PACS 104, medical imaging devices 106, and/or the database 108 may be hosted on-site at a facility (e.g., at a hospital) while the display optimization system 200 may be hosted at a remote site (e.g., on a cloud server).

Figure 2:
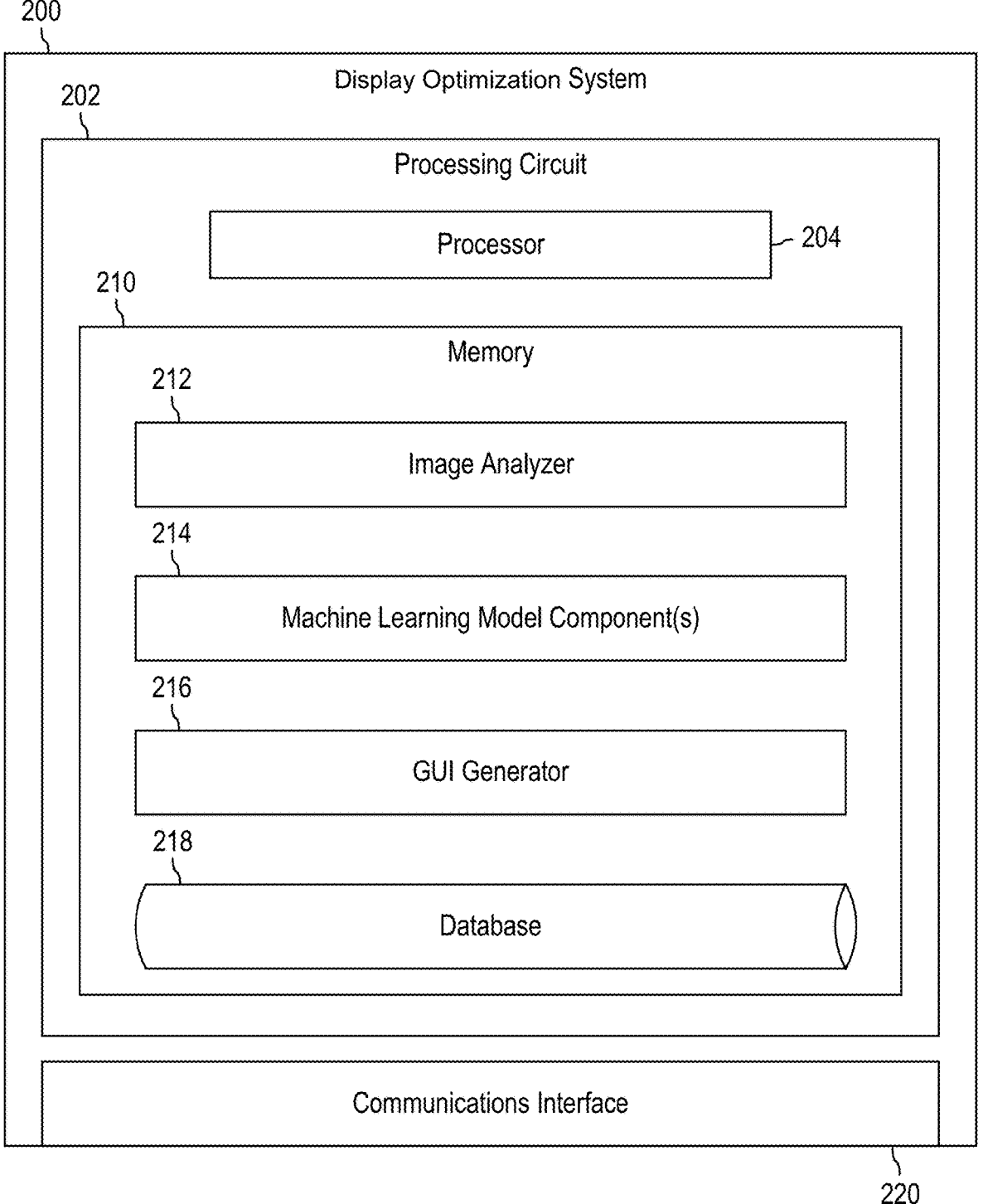
FIG. 2 is a block diagram of a display optimization system, in accordance with certain embodiments of the present disclosure.

Referring now to FIG. 2, a detailed block diagram of the display optimization system 200 is shown, according to some embodiments. Specifically, the display optimization system 200 is shown to include a processing circuit 202 that further includes a processor 204 and memory 210. The processor 204 can be a general-purpose processor, an application specific integrated circuit (ASIC), one or more field programmable gate arrays (FPGAs), a group of processing components, or other suitable electronic processing components. In some embodiments, the processor 204 is configured to execute program code stored on memory 210 to cause the display optimization system 200 to perform one or more operations. Memory 210 can include one or more devices (e.g., memory units, memory devices, storage devices, etc.) for storing data and/or computer code for completing and/or facilitating the various processes described in the present disclosure.

In some embodiments, the memory 210 includes tangible, computer-readable media that stores code or instructions executable by the processor 204. Tangible, computer-readable media refers to any media that is capable of providing data that causes the display optimization system 200 (i.e., a machine) to operate in a particular fashion. Example tangible, computer-readable media may include, but is not limited to, volatile media, non-volatile media, removable media and non-removable media implemented in any method or technology for storage of information such as computer readable instructions, data structures, program modules or other data. Accordingly, the memory 210 can include random access memory (RAM), read-only memory (ROM), hard drive storage, temporary storage, non-volatile memory, flash memory, optical memory, or any other suitable memory for storing software objects and/or computer instructions. The memory 210 can include database components, object code components, script components, or any other type of information structure for supporting the various activities and information structures described in the present disclosure. The memory 210 can be communicably connected to processor 204, such as via processing circuit 202, and can include computer code for executing (e.g., by the processor 204) one or more processes described herein.

While shown as individual components, it will be appreciated that the processor 204 and/or the memory 210 can be implemented using a variety of different types and quantities of processors and memory. For example, the processor 204 may represent a single processing device or multiple processing devices. Similarly, the memory 210 may represent a single memory device or multiple memory devices. Additionally, in some embodiments, the display optimization system 200 may be implemented within a single computing device (e.g., one server, one housing, etc.). In other embodiments, the display optimization system 200 may be distributed across multiple servers or computers (e.g., that can exist in distributed locations). For example, the display optimization system 200 may include multiple distributed computing devices (e.g., multiple processors and/or memory devices) in communication with each other that collaborate to perform operations.

The memory 210 is shown to include an image analyzer 212 configured to receive and preprocess image data. In some embodiments, the image analyzer 212 receives or retrieves image data from a database 218. As described herein, the database 218 may be configured to store and maintain image data. In some embodiments, the database 218 is internal to the display optimization system 200, as shown. In other embodiments, the database 218 is external to system 200. In some such embodiments, database 218 may be the same as, or functionally equivalent to, database 108, described above in connection with FIG. 1. In yet other embodiments, the database 218 may be distributed across multiple servers or computers (e.g., both the display optimization system 200 and the database 108). In any case, the image analyzer 212 may preprocess image data by first converting the image data into a suitable format, if necessary.

In some embodiments, the image analyzer 212 preprocesses image data (e.g., current and historical image data) by extracting features from the image data, although it will be appreciated that feature extraction may instead be performed by a machine learning model component 214 of the memory 210, as described below. Features, as known to those in the art, are individual measurable characteristics of the image data. In some embodiments, preprocessing the image data includes converting the image data to a 2-dimensional (2D), black and white image (e.g., from a 3D image); although it will also be appreciated that image data may initially be captured and stored as a black and white 2D image. In other embodiments, the image data is a 3D image that does not need to be converted to a 2D image. In some embodiments, preprocessing the image data includes smoothing of the image data. In some embodiments, the image analyzer 212 may perform a Z-transformation on the image data. In some embodiments, the image analyzer 212 may perform a histogram correction and/or stretching of the image data.

Once received and/or preprocessed, the display optimization system 200 may evaluate the image data using one or more machine learning model components 214 to identify features that can be used in a subsequent optimal anchor-prior matching operation. In some embodiments, for example, the machine learning model component(s) 214 may extract and analyze features from the image data (e.g., as opposed to image analyzer 212). The extracted features may be stored in association with the image data, for example, in a database 218 (e.g., in association with the image data, such as via a pointer or look-up table).

In some embodiments, the machine learning model component(s) 214 are configured to take as input raw DICOM metadata describing the image data (e.g., current and historical image data). In some examples, the DICOM metadata can describe device information (e.g., manufacturer, model, physical device properties, or the like), timestamp data, image orientation, and the like. The machine learning model component(s) 214 can process the image data (e.g., using a sequence tags extraction operation to extract information from image DICOM headers to generate new tags) and feed one or more required fields into the machine learning model component(s) 214 in order to identify anchor-prior image or series pairs, as discussed in more detail below. In particular, the machine learning model component(s) 214 can output match probabilities that are used to rank matches and create the lowest cost optimal pairing for all selected anchor image series. The viewer can then display the relevant prior image series in the same layout as the selected anchor image series. The inventors have confirmed that embodiments of the present disclosure are capable of accurately identifying matching and non-matching anchor-prior image series pairs with between 90%-95% accuracy.

As described herein, the machine learning model component(s) 214 may be or comprise a convolutional neural network (CNN), a transformer-based model, a recurrent neural network (RNN), a clustering model, a classification model, semi-supervised machine learning model, unsupervised machine learning model, combinations thereof, and/or the like.

The term "artificial intelligence" is defined herein to include the capability of a functional unit to perform functions that are generally associated with human intelligence such as reasoning and learning. AI includes, but is not limited to, knowledge bases, machine-learning, representation learning, and deep learning. The term "machine-learning" is defined herein to be a subset of AI that enables a machine to acquire knowledge by extracting patterns from raw data. Machine-learning techniques include, but are not limited to, logistic regression, support vector machines (SVMs), decision trees (including randomized decision forests), Naïve Bayes classifiers, and artificial neural networks. The term "representation learning" is defined herein to be a subset of machine-learning that enables a machine to automatically discover representations needed for feature detection, prediction, or classification from raw data. Representation learning techniques include, but are not limited to, autoencoders. The term "deep learning" is defined herein to be a subset of machine-learning that that enables a machine to automatically discover representations needed for feature detection, prediction, classification, etc. using layers of processing. Deep learning techniques include, but are not limited to, artificial neural network (including deep nets, long short-term memory (LSTM) recurrent neural network (RNN) architecture), or multilayer perceptron (MLP). Machine-learning models include supervised, semi-supervised, and unsupervised learning models. In a supervised learning model, the model learns a function that maps an input (also known as feature or features) to an output (also known as a target or target) during training with a labeled data set (or dataset). In an unsupervised learning model, the model learns a function that maps an input (also known as feature or features) to an output during training with an unlabeled data set. In a semi-supervised model, the model learns a function that maps an input (also known as feature or features) to an output (also known as a target or target) during training with both labeled and unlabeled data. In some instances, the AI may comprise natural language processing (NLP). NLP refers to a branch of AI concerned with giving computers the ability to understand text and spoken words in much the same way human beings can.

In some embodiments, the machine learning model component(s) 214 may first (e.g., prior to analyzing new DICOM data) be trained using a known (e.g., "training") set of data. The training data can include labeled historical image data, display information, DICOM information and/or metadata, associated with the historical image data. For example, the training data may be a dataset that includes multiple images and their corresponding DICOM metadata for a plurality of vendors. The training data set may comprise labeled data that is iteratively reviewed by medical providers to provide a representative data set. In various examples, the machine learning model component(s) 214 are trained on sufficiently varied data to capture variations to be able to efficiently extrapolate and interpolate for new inputs. In some embodiments, the machine learning model component(s) 214 can utilize image pixel-based matching to identify examples of historical image data that are similar to new or current image data. A pixel-based matching operation may utilize features that represent relationships between multiple pixels or groupings of pixels within images. Such examples thus avoid the curse of DICOM heterogeneity and empty fields.

For example, rule-based techniques are unsuitable for identifying similar images to a target image in an instance in which the metadata associated with the target image lacks specificity or has missing fields. By way of example, different technicians may input information or tag an image to indicate "axial orientation" in a plurality of ways including "AxialT1," "AX," "AXT1," "AX T1." Accordingly, a current series may have a first tag or value, and a relevant prior image series may have a different tag or value associated therewith. In contrast with existing rule-based techniques which rely on identifying exact matches, the machine learning model component(s) disclosed herein can use flexible internal rule sets to output valuable matches, even in instances where match probabilities are low.

Once trained, the machine learning model component(s) 214 can be configured to perform an optimal anchor-prior matching operation on at least a portion of the new image data (e.g., one or more current or anchor image series, such as, but not limited to, MRI scans) and at least a portion of the historical image data (e.g., one or more prior image series) in order to output at least one optimal anchor-prior pair of images. The at least one optimal anchor-prior image pair or series pair may be used within a display protocol.

Memory 210 is also shown to include a graphical user interface (GUI) generator 216. The GUI generator 216 may be configured to generate and display (e.g., or cause a remote device, such as PACS 104, to display) any number of graphical user interfaces (GUIs). In particular, the GUI generator 216 may generate and/or display GUIs that include images (e.g., generated from image data) from at least one optimal anchor-prior image pair or series pair identified by performing an optimal anchor-prior matching operation using the machine learning model component(s) 214. A display protocol may define a set of rules or instructions that determine how the images (e.g., at least one anchor-prior image pair or series) should be displayed, and the layout of said images (e.g., on PACS 104). In some embodiments, a GUI is generated and/or image data is retrieved responsive to a user request to view a particular image or study. For example, a medical professional may "request" to view a study by logging into the PACS 104 and/or selecting the study from PACS 104.

Still referring to FIG. 2, system 200 is also shown to include a communications interface 220. Communications interface 220 may facilitate communications between system 200 and any of the components described above in FIG. 1. For example, communications interface 220 can provide means for transmitting data to, or receiving data from, PACS 104, medical imaging devices 106, and the database 108. Accordingly, the communications interface 220 can be or can include a wired or wireless communications interface (e.g., jacks, antennas, transmitters, receivers, transceivers, wire terminals, etc.) for conducting data communications. In various embodiments, communications via communications interface 220 may be direct (e.g., local wired or wireless communications) or via a network (e.g., a WAN, the Internet, a cellular network, etc.), such as the network 102. For example, the communications interface 220 can include a Wireless Fidelity (WiFi) transceiver for communicating via a wireless communications network. In another example, the communications interface 220 may include cellular or mobile phone communications transceivers. In yet another example, communications interface 220 may include a low-power or short-range wireless transceiver (e.g., Bluetooth®).

Referring now to FIG. 3, a flow diagram of an example method 300 that includes performing an optimal anchor-prior matching operation that can be used in turn to generate (e.g., output) user interface data for display in conjunction with a display protocol is provided. In various examples, the method 300 advantageously automates the identification of the most relevant medical image data with little to no human input, which makes related workflows faster and more efficient. In some embodiments, the method 300 is implemented by the system 100, as described above. More specifically, in some embodiments, the method 300 can be implemented at least in part by the display optimization system 200. It will be appreciated that certain steps of the method 300 may be optional and, in some embodiments, the method 300 may be implemented using less than all of the steps.

Beginning at step/operation 302, the display optimization system (such as, but not limited to, the display optimization system 200 described above in connection with FIG. 2) receives new image data (e.g., an anchor image series or current series). In some embodiments, the new image data comprises one or more medical images (e.g., pictures or scans) such as MRI, CT, US, or X-ray images. The new image data may be in the form of a black-and-white, 2D image, and any corresponding metadata (e.g., raw DICOM metadata). In some embodiments, however, the new image data includes 3D images. In some embodiments, the new image data is received from one or more medical imaging devices 106 (e.g., such as, but not limited to, medical imaging devices 106), pre-processed by the display optimization system 200, and stored in a database (e.g., database 108 and/or database 218). In some embodiments, the new image data is processed in real-time or near real-time.

Subsequent to step/operation 302, the method 300 proceeds to step/operation 304. Optionally, at step/operation 304, the display optimization system extracts one or more features from the data (e.g., raw DICOM metadata, pixel data, combinations thereof, and/or the like) associated with the new image data. In some embodiments, the one or more features can include display features associated with the image (e.g., axial, sagittal, coronal). In some implementations, the one or more features include direct or derivative features from DICOM metadata such as pulse sequence information, contrast use, image type, sequence timings, echo type, projection, diffusion coefficient, frame type, kernel, laterality and/or the like. It should be understood that step/operation 304 can be performed in response to new image data being transmitted from a medical imaging device. For example, the display optimization system can process received image data, extract one or more features, and store the image data and extracted features in a database until it is required or requested, such as by being selected for review or evaluation by a radiologist.

Subsequent to step/operation 304, the method 300 proceeds to step/operation 306. At step/operation 306, the display optimization system receives an indication of a selected anchor study comprising one or more anchor image series. For example, a radiologist can select to review or evaluate an anchor study via a PACS. In some examples, the selected anchor study comprises at least some of the new image data received and processed in step/operation 302 and step/operation 304.

At step/operation 308, the display optimization system retrieves historical image data (e.g., a prior study comprising one or more prior image series) corresponding with the selected anchor study comprising one or more anchor image series. In some examples, the historical image data can be manually selected by a radiologist or could be automatically selected based at least on a display protocol defined by the radiologist. In some implementations, the historical image data is automatically identified based on the one or more extracted features at step/operation 304 and/or common features associated with each of the historical image data and the new image data.

Subsequent to step/operation 308, the method 300 proceeds to step/operation 310. At step/operation 310, the display optimization system performs, using one or more machine learning model component(s), an optimal anchor-prior matching operation based at least on the one or more extracted features associated with the one or more anchor image series and the one or more prior image series. An output of the optimal anchor-prior matching operation is at least one optimal anchor-prior image pair or series pair from the one or more anchor image series and the historical image data (e.g., one or more prior image series). In some implementations, step/operation 310 can occur in real-time in response to a radiologist reviewing a study or when image data is initially received by the PACS. In some implementations, pairing information can be generated and stored for later retrieval when requested by a radiologist.

In some embodiments, the display optimization system utilizes extracted features (e.g., raw DICOM metadata) for an anchor or current series and feeds required fields into one or more machine learning model components. The machine learning model component(s) can use the extracted features to identify optimal pairings of anchor image series to prior image series from a selected anchor study and identified prior study. The machine learning model component(s) can be configured to output match probabilities that are used to rank matches and create a lowest cost optimal pairing for all selected anchor image series. In some embodiments, the display optimization system ranks each anchor image series (e.g., 1-N) of a selected anchor study to each prior image series (e.g., 1-M) of the identified prior study and outputs the top ranking image series pairings (e.g., via a display). In some embodiments, the machine learning model component(s) selects one or more images that satisfy one or more pre-determined characteristics. The pre-determined characteristics can include image characteristics (e.g., image quality, image orientation), location characteristics (e.g., a target location or area of the body), pulse sequence characteristics, and/or the like. In some embodiments, the machine learning model(s) can identify relevant or similar images using a pixel-based matching operation. In some embodiments, the machine learning model component(s) can comprise a CNN configured to take the image data (e.g., anchor image series) as an input and extract one or more features using a feature extraction network, such as convolutional layer(s) and/or pooling layer(s). The convolutional layer(s) may include a plurality of digital filters for performing a convolution operation on the image data. The pooling layer(s) may dimensionally reduce the input image data and may also set a threshold for feature extraction.

Optionally, subsequent to step/operation 310, the method 300 proceeds to step/operation 312. At step/operation 312, the display optimization system generates user interface data based at least on the at least one optimal anchor-prior image pair or series pair. In some embodiments, the display optimization system further identifies (e.g., retrieves) a display protocol (e.g., rule-based display protocol or hanging protocol) associated with a user request to view at least a portion of the new image data (e.g., one or more anchor image series) for generating the user interface data. As noted herein, the display protocol may be a set of instructions defining how images should be displayed (e.g., a selection, sequence, order, layout, combinations thereof, and/or the like).

For example, the display optimization system can provide (e.g., send, transmit) instructions for generating user interface data that includes anchor-prior image pairs in accordance with the display protocol. In various examples, the display protocol may define a selection of images and a corresponding organization, order and/or location for presentation within a user interface/GUI. In particular, a PACS 104 may be configured to display at least a portion of the image data (e.g., at least one anchor-prior image pair or series pair) in response to a user request. For example, a physician or other medical professional may access a PACS 104 and may retrieve a new study, which in turn causes the display optimization system to identify optimal image pairs from prior studies associated therewith (e.g., based on DICOM metadata and/or a pixel-based matching operation). The PACS 104 can output the optimal image pairs within a stored/retrieved display protocol via a user interface.

Referring now to FIG. 4A, a table 400 depicting an example output of a machine learning model. In particular, FIG. 4A shows an example model output ranking for a plurality of anchor image series (A1, A2, and A3) and a plurality of prior image series (P1, P2, P3, and P4) where a score (between 0 and 1) is generated for each candidate pairing. In the example shown in FIG. 4A, a higher score (close to 1) is indicative of a high or positive degree of correspondence between the pairing, and a lower score (close to 0) is indicative of a low or negative degree of correspondence between the pairing. As shown, the A1-P1 pairing has a score of 0.9, the A1-P2 pairing has a score of 0.5, the A1-P3 pairing has a score of 0.6, and the A1-P4 pairing has a score of 0.1. Accordingly, the A1-P1 pairing is the optimal anchor-prior image series match for anchor image series A1.

As further depicted, the A2-P1 pairing has a score of 0.7 the A2-P2 pairing has a score of 0.4, the A2-P3 pairing has a score of 0.8, and the A2-P4 pairing has a score of 0.3. Accordingly, the A2-P3 pairing is the optimal anchor-prior image series match for anchor image series A2.

Additionally, as illustrated, the A3-P1 pairing has a score of 0.9, the A3-P2 pairing has a score of 0.3, the A3-P3 pairing has a score of 0.5, and the A3-P4 pairing has a score of 0.8. Accordingly, the A3-P1 pairing is the optimal anchor-prior image series match for anchor image series A3.

In the example shown in FIG. 4A, A1 and A3 are both matched to P1. In such examples, an additional optimal selection mechanism can be implemented to shift the pairing from A3-P1 to A3-P4 based on the lowest global scoring.

By implementing the above-noted operations, user interface data can be generated and presented in a manner that increases the efficiency of imaging systems, such as PACS 104, by identifying optimal images for presentation without extensive input by an end-user (e.g., searching or manual configuration of a viewport).

Figure 4B:
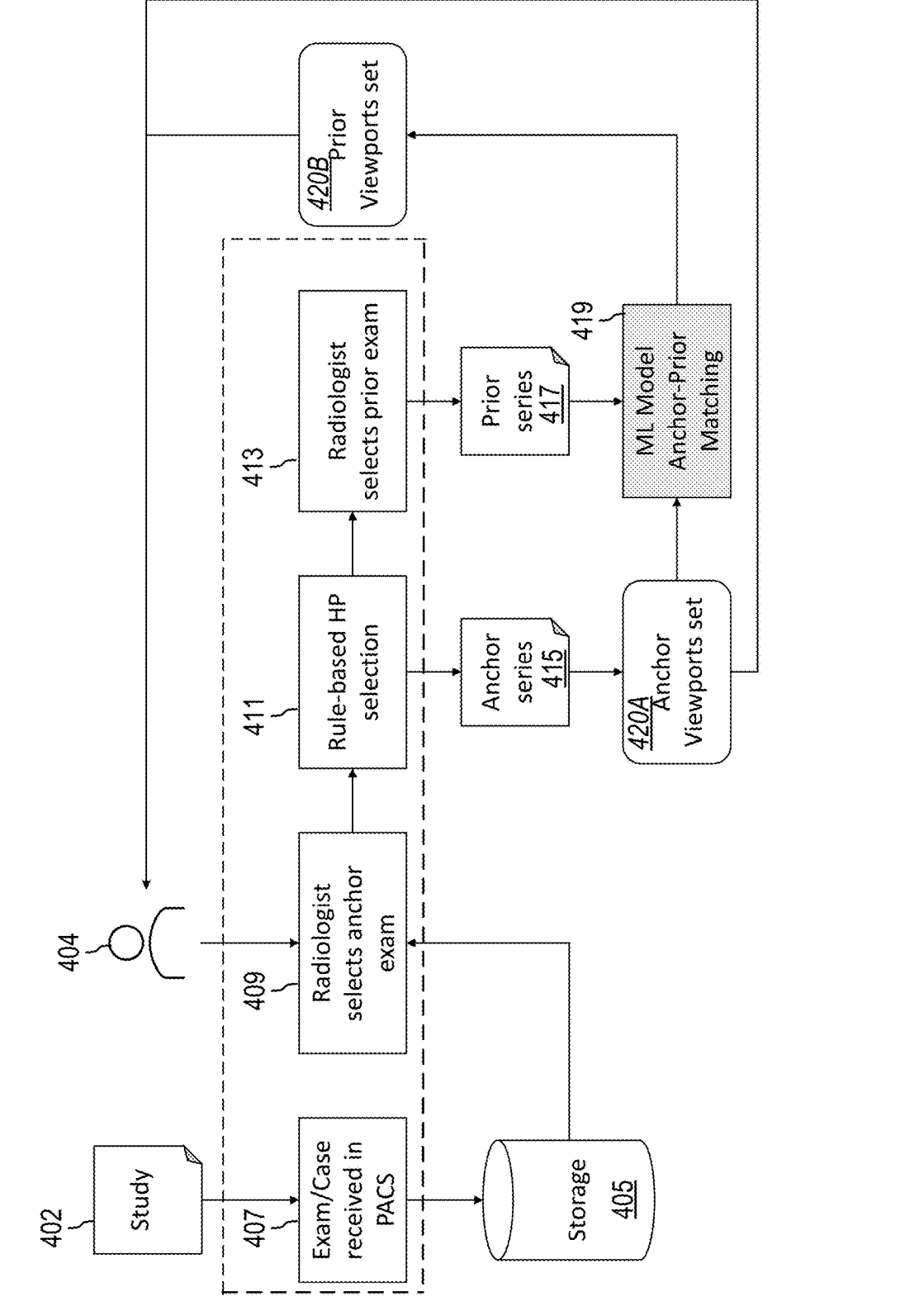
FIG. 4B is a workflow of a process for performing an optimal anchor-prior matching operation and generating user interface data, in accordance with certain embodiments of the present disclosure.

Referring now to FIG. 4B, a schematic diagram depicting a workflow 401 for implementing certain embodiments of the present disclosure is provided.

In various implementations, at step/operation 407, a study 402 (e.g., anchor image series) is received by a PACS. As shown, the PACS is in communication with one or more databases 405. A medical provider (e.g., radiologist) may access the PACS via a user computing entity and/or graphical user interface. The one or more databases 405 can store medical image data (e.g., new image data, historical image data, and the like) obtained from one or more medical imaging devices (e.g., x-rays, MRIs, CTs, and the like).

As illustrated, at step/operation 409, the medical provider (e.g., radiologist 404) selects or requests to view a study 402 (e.g., selects one or more anchor studies) via the user computing entity and/or graphical user interface.

At step/operation 411, in some embodiments, based at least on the selection of the study 402, one or more rule-based display protocols may be identified and/or applied.

Subsequent to step/operation 411, at step/operation 413, the medical provider (e.g., radiologist) selects one or more prior studies. The system retrieves one or more anchor image series 415 and one or more prior image series 417 based at least in part on the selection of the one or more anchor studies and the one or more prior studies at step/operation 409 and step/operation 413.

Then, at step/operation 419, one or more machine learning model components are applied to the anchor image series 415 and the prior image series 417 to identify at least one optimal anchor-prior image pair or series pair. For example, the system may perform an optimal anchor-prior matching operation by analyzing DICOM metadata associated with each of the anchor image series 415 and prior image series 417 to output a plurality of anchor-prior image pairs or series pairs. Subsequently, the system generates and outputs user interface data, as shown anchor viewports set 420A and prior viewports set 420B, based at least on the identified anchor-prior image pairs or series pairs for display via the graphical user interface.

Figure 5:
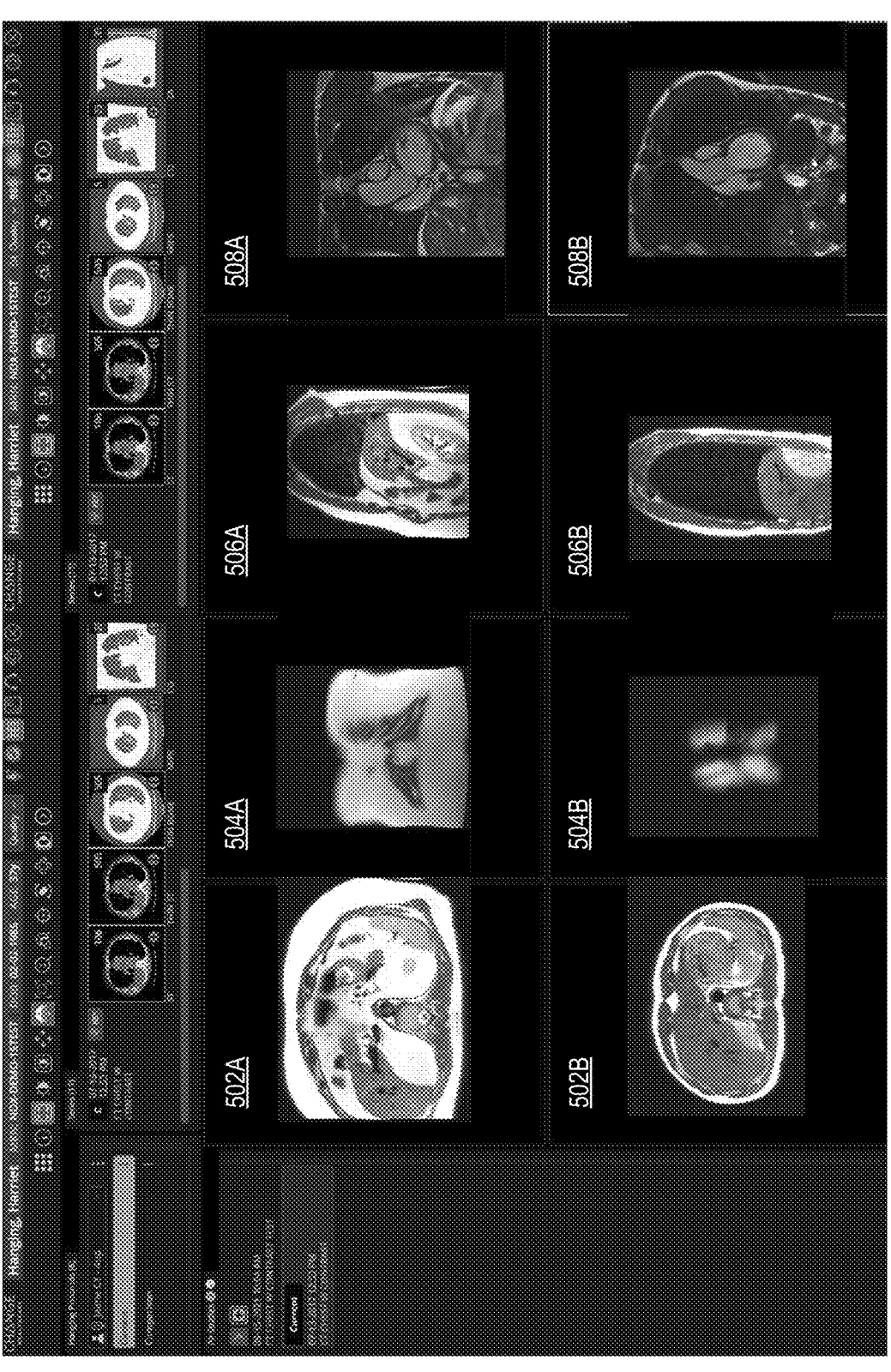
FIG. 5 is an operational example of a user interface, in accordance with certain embodiments of the present disclosure.

Referring now to FIG. 5, an operational example depicting a user interface 500 that may be generated based at least in part on an output of an optimal anchor-prior matching operation is provided. A display optimization system including one or more machine learning model components may generate the user interface data and present (e.g., transmit, send, and/or the like) corresponding user interface data for presentation via the user interface 500.

As depicted in FIG. 5, the user interface 500 depicts an anchor study comprising a first plurality of image series 502A, 504A, 506A, and 508A. Each image series (e.g., image series 502A) can in turn comprise multiple images and the user can scroll through the image series to view different images. Additionally, the user interface 500 depicts a prior study comprising a second plurality of image series 502B, 504B, 506B, and 508B. As shown, each of the first plurality of image series from the anchor study is associated with a respective image series from the prior study (e.g., image series 502A corresponds with image series 502B, image series 504A corresponds with image series 504B, and so on), where each image series pair depicts a particular location, area, and/or view. In various examples, an end user may access the user interface data using user-selectable interface elements.

Additionally, the user interface 500 may comprise various additional features and functionalities for accessing, and/or viewing user interface data. The user interface 500 may also comprise messages to an end-user in the form of banners, headers, notifications, and/or the like. As will be recognized, the described elements are provided for illustrative purposes and are not to be construed as limiting the dynamically updatable interface in any way.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied, and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions, and arrangement of the exemplary embodiments without departing from the scope of the present disclosure.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products including machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures, and which can be accessed by a general purpose or special purpose computer or other machine with a processor.

When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general-purpose computer, special purpose computer, or special purpose processing machines to perform a certain function or group of functions.

Although the figures show a specific order of method steps, the order of the steps may differ from what is depicted. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule-based logic and other logic to accomplish the various connection steps, processing steps, comparison steps and decision steps.

It is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc., of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

What is claimed is:

1. A computer-implemented method for identifying at least one optimal anchor-prior image pair or series pair, the computer-implemented method comprising:

receiving, by one or more processors, new medical imaging data;

extracting, by the one or more processors, one or more features from the new medical imaging data;

receiving, by the one or more processors, an indication of a selected anchor study comprising one or more anchor image series, wherein the selected anchor study comprises at least some of the new medical imaging data;

retrieving, by the one or more processors, a prior study comprising one or more prior image series corresponding with the selected anchor study;

performing, by the one or more processors and using one or more machine learning model components, an optimal anchor-prior matching operation based at least on the extracted one or more features associated with the one or more anchor image series and the one or more prior image series; and outputting, by the one or more processors, the at least one optimal anchor-prior image pair or series pair.

2. The computer-implemented method of claim 1, further comprising:

retrieving, by the one or more processors, a display protocol; and generating, by the one or more processors, user interface data based at least on the display protocol and the at least one optimal anchor-prior image pair or series pair.

3. The computer-implemented method of claim 2, wherein the display protocol defines at least one of a selection, layout, or order of images for presentation within a user interface.

4. The computer-implemented method of claim 1, wherein the new medical imaging data comprises Digital Imaging and Communications in Medicine (DICOM) metadata, and wherein the one or more features are extracted from the DICOM metadata.

5. The computer-implemented method of claim 4, wherein performing the optimal anchor-prior matching operation comprises performing pixel-based matching on the one or more anchor image series and the one or more prior image series.

6. The computer-implemented method of claim 1, wherein the one or more machine learning model components are trained using labeled historical image data.

7. The computer-implemented method of claim 1, wherein the one or more machine learning model components include at least one of a convolutional neural network (CNN), a transformer-based model, a recurrent neural network (RNN), a clustering model, a classification model, a semi-supervised machine learning model, or an unsupervised machine learning model.

8. The computer-implemented method of claim 1, wherein performing the optimal anchor-prior matching operation comprises identifying at least one image that satisfies at least one of image characteristics, location characteristics, or pulse sequence characteristics.

9. The computer-implemented method of claim 8, wherein the image characteristics are associated with at least one of image quality or image orientation.

10. A display optimization system comprising:

one or more processors; and one or more memories storing processor-executable instructions that, when executed by the one or more processors, cause the one or more processors to perform operations comprising:

receiving new medical imaging data;

extracting one or more features from the new medical imaging data;

receiving an indication of a selected anchor study comprising one or more anchor image series, wherein the selected anchor study comprises at least some of the new medical imaging data;

retrieving a prior study comprising one or more prior image series corresponding with the selected anchor study;

performing, using one or more machine learning model components, an optimal anchor-prior matching operation based on the extracted one or more features associated with the one or more anchor image series and the one or more prior image series; and outputting at least one optimal anchor-prior image pair or series pair.

11. The display optimization system of claim 10, wherein the operations further comprise:

retrieving a display protocol; and generating user interface data based at least on the display protocol and the at least one optimal anchor-prior image pair or series pair.

12. The display optimization system of claim 11, wherein the display protocol defines at least one of a selection, layout, or order of images for presentation within a user interface.

13. The display optimization system of claim 10, wherein the new medical imaging data comprises Digital Imaging and Communications in Medicine (DICOM) metadata, and wherein the one or more features are extracted from the DICOM metadata.

14. The display optimization system of claim 10, wherein performing the optimal anchor-prior matching operation includes:

performing pixel-based matching on the one or more anchor image series and the one or more prior image series.

15. The display optimization system of claim 10, wherein the one or more machine learning model components are trained using labeled historical image data.

16. The display optimization system of claim 10, wherein the one or more machine learning model components include a convolutional neural network (CNN), a transformer-based model, a recurrent neural network (RNN), a clustering model, a classification model, an semi-supervised machine learning model, or an unsupervised machine learning model.

17. The display optimization system of claim 10, wherein performing the optimal anchor-prior matching operation includes:

identifying at least one image that satisfies at least one of image characteristics, location characteristics, timestamp characteristics, or pulse sequence characteristics.

18. One or more non-transitory, computer-readable media storing processor-executable instructions that, when executed by one or more processors, cause the one or more processors to perform operations comprising:

receiving new medical imaging data;

extracting one or more features from the new medical imaging data;

receiving an indication of a selected anchor study comprising one or more anchor image series, wherein the selected anchor study comprises at least some of the new medical imaging data;

retrieving a prior study comprising one or more prior image series corresponding with the selected anchor study;

performing, using one or more machine learning model components, an optimal anchor-prior matching operation based at least on the extracted one or more features associated with the one or more anchor image series and the one or more prior image series; and outputting at least one optimal anchor-prior image pair or series pair.

19. The one or more non-transitory, computer-readable media of claim 18, wherein the operations further comprise:

retrieving a display protocol; and generating user interface data based at least on the display protocol and the at least one optimal anchor-prior image pair or series pair.

20. The one or more non-transitory, computer-readable media of claim 18, wherein the new medical imaging data comprises Digital Imaging and Communications in Medicine (DICOM) metadata, and wherein the one or more features are extracted from the DICOM metadata.

* * * * *